United States Patent
Kuhr et al.

(10) Patent No.: US 7,322,998 B2
(45) Date of Patent: *Jan. 29, 2008

(54) DEVICE FOR WITHDRAWING BLOOD FOR DIAGNOSTIC APPLICATIONS

(75) Inventors: Hans Jurgen Kuhr, Mannheim (DE); Richard Forster, Pfreimd (DE)

(73) Assignee: Roche Diagnostics GmbH, Mannheim (DE)

( * ) Notice: Subject to any disclaimer, the term of this patent is extended or adjusted under 35 U.S.C. 154(b) by 215 days.

This patent is subject to a terminal disclaimer.

(21) Appl. No.: 11/213,164

(22) Filed: Aug. 26, 2005

(65) Prior Publication Data

US 2005/0288637 A1    Dec. 29, 2005

Related U.S. Application Data

(63) Continuation of application No. 10/189,928, filed on Jul. 3, 2002, now Pat. No. 7,077,828, which is a continuation-in-part of application No. 09/518,799, filed on Mar. 3, 2000, now Pat. No. 6,419,661.

(30) Foreign Application Priority Data

Mar. 5, 1999    (DE) .................................. 199 09 602

(51) Int. Cl.
    *A61B 17/32*    (2006.01)
(52) U.S. Cl. ........................ 606/182; 606/181
(58) Field of Classification Search ............... 606/181, 606/182, 156, 157; 401/221, 211; 30/366
    See application file for complete search history.

(56) References Cited

U.S. PATENT DOCUMENTS

| 3,030,959 | A | 4/1962 | Grunert |
| 3,244,317 | A | 4/1966 | Raybin |
| 3,696,915 | A | 10/1972 | Douglas |
| 3,833,146 | A | 9/1974 | Braginetz |
| 4,203,446 | A | 5/1980 | Höfert et al. |
| 4,442,836 | A | 4/1984 | Meinecke et al. |
| 4,469,110 | A | 9/1984 | Slama |
| 4,535,769 | A | 8/1985 | Burns |

(Continued)

FOREIGN PATENT DOCUMENTS

DE    2803345 B1    6/1979

(Continued)

*Primary Examiner*—Patricia Bianco
*Assistant Examiner*—Camtu Nguyen
(74) *Attorney, Agent, or Firm*—Bose McKinney & Evans, LLP (57) ABSTRACT

A device for withdrawing blood for diagnostic purposes including a lancet and a lancet drive having a loadable elastic drive spring provided within an elongated housing. A relaxing motion of the drive spring is converted into a puncturing motion to move the lancet at high speed in a puncturing direction until its tip exits out of an opening of the housing. The device includes a transmission in the housing that has an input side that transforms the motion of a loading element along a linear loading path into a rotational motion of a lancet drive rotor to load the lancet drive rotor by tensioning the drive spring. When the lancet drive is triggered, the output side of the transmission converts a rotational motion of the lancet drive rotor, driven by the drive spring, into the puncturing motion in a direction along the main axis.

27 Claims, 6 Drawing Sheets

U.S. PATENT DOCUMENTS

| | | |
|---|---|---|
| 4,653,513 A | 3/1987 | Dombrowski |
| 4,735,203 A | 4/1988 | Ryder et al. |
| 4,794,926 A | 1/1989 | Munsch et al. |
| 4,817,603 A | 4/1989 | Turner et al. |
| 4,821,878 A | 4/1989 | Jones |
| 4,860,937 A | 8/1989 | Arnold |
| 4,895,147 A | 1/1990 | Bodicky et al. |
| 4,924,879 A | 5/1990 | O'Brien |
| 4,998,452 A | 3/1991 | Blum |
| 5,035,704 A | 7/1991 | Lambert et al. |
| 5,152,775 A | 10/1992 | Ruppert |
| 5,196,025 A | 3/1993 | Ranalleta et al. |
| 5,269,800 A | 12/1993 | Davis, Jr. |
| 5,304,193 A | 4/1994 | Zhadanov |
| 5,318,584 A | 6/1994 | Lange et al. |
| 5,464,418 A | 11/1995 | Schraga |
| 5,478,345 A | 12/1995 | Stone et al. |
| 5,514,152 A | 5/1996 | Smith |
| 5,527,334 A | 6/1996 | Kanner et al. |
| 5,531,763 A | 7/1996 | Mastri et al. |
| 5,554,166 A | 9/1996 | Lange et al. |
| 5,632,410 A | 5/1997 | Moulton et al. |
| 5,643,306 A | 7/1997 | Schraga |
| 5,662,669 A | 9/1997 | Abidin et al. |
| 5,829,589 A | 11/1998 | Nguyen et al. |
| 5,908,434 A | 6/1999 | Schraga |
| 5,951,582 A | 9/1999 | Thorne et al. |
| 6,197,040 B1 | 3/2001 | LeVaughn et al. |
| 6,358,265 B1 | 3/2002 | Thorne, Jr. et al. |
| 6,472,220 B1 | 10/2002 | Simons et al. |
| 6,514,270 B1 | 2/2003 | Schraga |
| 6,719,771 B1 | 4/2004 | Crossman |
| 2003/0050656 A1 | 3/2003 | Schraga |
| 2004/0039407 A1 | 2/2004 | Schraga |

FOREIGN PATENT DOCUMENTS

| | | |
|---|---|---|
| EP | 0 565 970 A1 | 10/1993 |
| WO | WO 98/14125 | 9/1998 |

DEVICE FOR WITHDRAWING BLOOD FOR DIAGNOSTIC APPLICATIONS

RELATED PATENTS

This application is a continuation of application Ser. No. 10/189,928, filed Jul. 3, 2002, now U.S. Pat. No. 7,077,828, which in turn is a continuation-in-part of application Ser. No. 09/518,799, filed Mar. 3, 2000, now U.S. Pat. No. 6,419,661.

FIELD OF THE INVENTION

The present invention concerns a blood lancet device for withdrawing blood for diagnostic purposes.

BACKGROUND AND SUMMARY OF THE INVENTION

Lancets are used in diagnostic applications to withdraw a small amount of blood by pricking a part of the body (usually the finger or the ear-lobe). In the past, the puncturing procedure had been carried out by trained, specially educated personnel either manually or using a simple apparatus. This method to obtain a blood sample is acceptable when blood investigations must only be carried out occasionally, since in this case the pain associated with the puncturing does not play a decisive role.

The requirements for blood withdrawal are substantially more stringent when regular monitoring of certain analytic values in the blood of a patient is necessary. This is particularly the case for diabetics whose blood sugar levels must be monitored frequently and regularly in order to keep these levels (which depend on food ingestion, physical activity and other factors) within certain limiting values through the administration of insulin injections. Such an intensive blood sugar therapy is of extreme importance to the health of the patient and requires at least four blood withdrawals per day. For example, the publication "The Effect of Intensive Treatment of Diabetes on the Development and Progressing of Long-term Complications in Insulin-dependent Diabetes Mellitus," of the Diabetes Control and Complications Trial Research Group, New England Journal of Medicine, 1993, 977 to 986 reports that intensive therapy, involving at least four blood samples per day, can reduce the probability of retinopathy (which eventually leads to blinding of the patient) by 76%. This is also the case for other serious long term damage associated with diabetes mellitus.

Long-term intensive blood sugar therapy is only feasible by so-called "home-monitoring," carried out by the patient himself or by family members without the use of trained medical personnel. The willingness and ability of the patient to obtain a blood sample by means of a lancet at least four times daily depends decisively on the properties of the blood withdrawal device. It is desirable that the pain associated with generation of the wound necessary for blood withdrawal is as low as possible. It is also desirable that the device be as simple to operate as possible, since a large share of the patients are, due to their illness or advanced age, not capable of carrying out difficult manual operations in a precise fashion. In addition, low weight and a practical shape are desirable in order that the device can be easily carried along with the patient. Also, the design should be as simple as possible, durable, and inexpensive.

Blood withdrawal devices and associated lancets have been proposed having various structural configurations to satisfy these design parameters. They are described, by way of example, in the following U.S. Pat. Nos. 4,442,836; 4,535,769; 4,469,110; 4,653,513; 4,895,147; 4,924,879; 5,318,584; 5,554,166. Although these known designs provide substantial improvements in blood withdrawal for diagnostic purposes, they are inadequate for various reasons. In particular, those devices which produce the wound with very low pain levels have disadvantages with regard to handling and/or shape and size of the device. Conversely, small and easily operated devices are typically associated with insufficiently low pain levels.

The present invention provides a device for withdrawing blood for diagnostic applications, comprising an elongated housing on the front end of which an exit opening is provided for the tip of a lancet, a lancet which can be displaced within the housing in the direction of its main axis along a predetermined puncture path, a lancet guide for guiding the lancet along the predetermined puncture path and a lancet drive having a resilient drive spring which can be locked in a loaded state using a locking device and which converts the relaxing motion of the drive spring into a puncture motion after the locking device is released, wherein the lancet is moved with high velocity along the predetermined puncture path in the puncture direction until its tip exits out of the exit opening to produce a wound in a part of the body proximate the exit opening, and wherein a two-sided rotary/translatory transmission is provided in the housing for converting the motion of a loading element movable along a linear loading path into a rotational motion of a lancet drive rotor which rotates about a rotational axis running parallel to the axis of the device to load the lancet drive rotor by tensioning the drive spring, and for converting, after release of the lancet drive, a rotational motion of the lancet drive rotor driven by the drive spring into the puncturing motion in the direction of the main axis.

The present invention also provides a blood withdrawal kit comprising the following mutually adapted system components: a blood withdrawal device in accordance with the invention and lancets adapted to be held in and used with the device. Such blood withdrawal kits (which also can be referred to as blood withdrawal equipment) are initially sold in the form of a packaged unit containing both system components. Since the lancets can normally be used only once, they are also provided in separate packages for use by patients already having blood withdrawal devices.

The term "transmission" is to be understood in its general sense (i.e., in terms of a kinematic device for coupling and converting motion). In the present case, the double sided rotary/translatory transmission transforms a translation motion of the loading element into a rotational motion of the lancet drive rotor and a rotational motion of the lancet drive rotor into a translational motion of the lancet.

Embodiments of the invention should take into consideration the fact that a low-pain puncture requires a very rapid and precise puncturing motion. To this end, it is desirable that the drive spring have a high spring constant. On the other hand, the loading element should be sufficiently easy to operate such that older and physically handicapped people can load the blood withdrawal device.

In accordance with one embodiment of the invention, the lancet drive rotor comprises a surface running along a helical path and the loading element comprises a loading cam having a contact surface that moves on the surface of the helical path to convert a linear motion of the loading element into a rotational motion of the lancet drive rotor. The helical path may be formed on a loading sleeve that operates in cooperation with the drive rotor. The forward end of the loading sleeve facing the exit opening may be designed to surround a lancet holder holding the lancet.

In accordance with another embodiment of simple construction and having low vibration, a guiding cam is provided in proximity to the front end of the transmission. It controls, in cooperation with a guide pin provided on the lancet holder, the puncturing motion and the return motion of the lancet holder and the lancet contained therein. Control of the puncturing and return motions through cooperation between a guide pin and a guide cam is disclosed in the above-mentioned U.S. Pat. Nos. 5,318,584 and 5,554,106.

These and other features of the present invention described above, will be readily apparent to those skilled in the art upon reference to the following description and the accompanying drawings.

DETAILED DESCRIPTION OF EMBODIMENTS OF THE INVENTION

The embodiments described below are merely exemplary and are not intended to limit the invention to the precise forms disclosed. Instead, the embodiments were selected for description to enable one of ordinary skill in the art to practice the invention.

Figure 1:
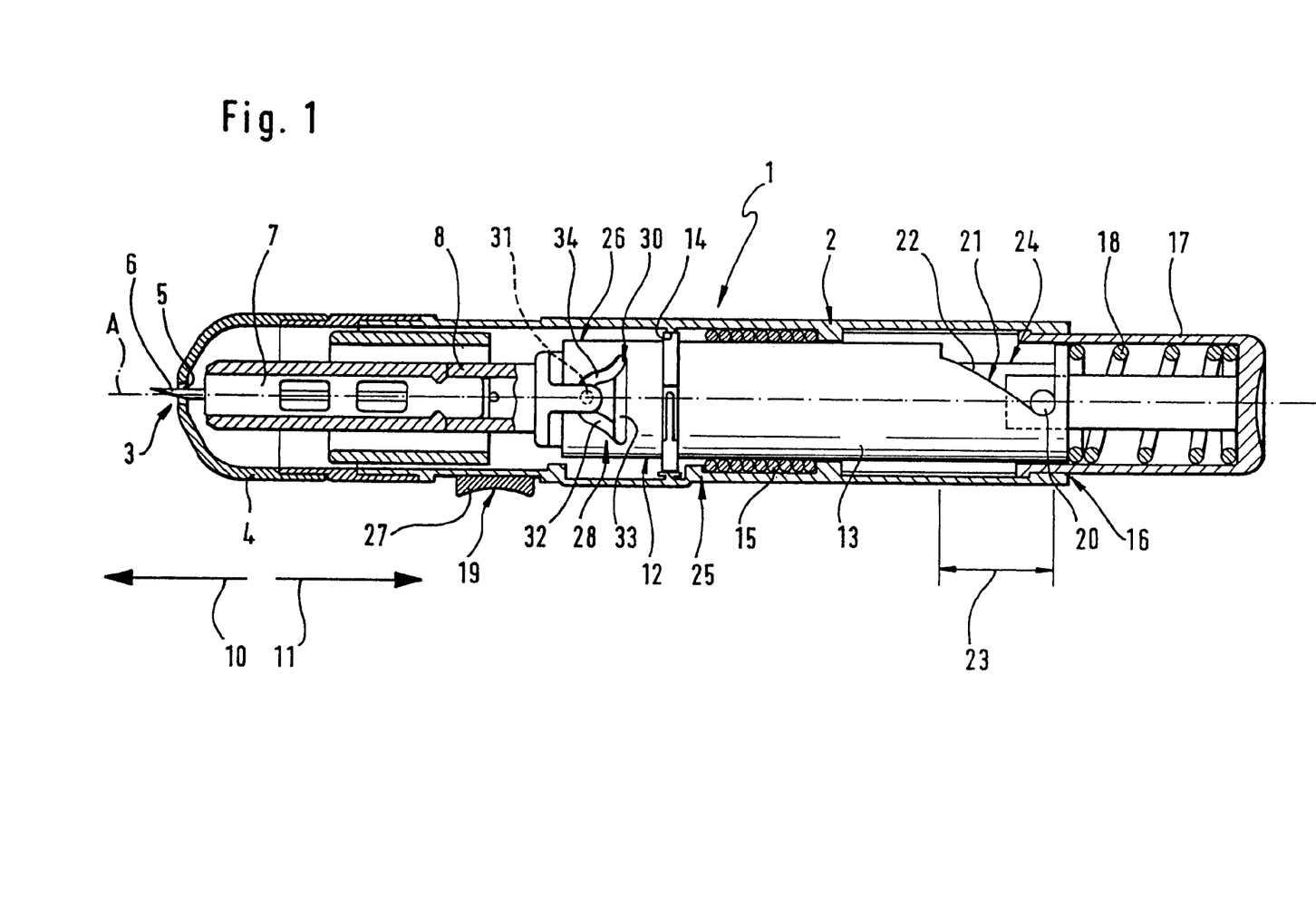
FIG. 1 is a side view, partly in section, of a blood withdrawal device according to one embodiment of the invention.

The blood withdrawal device 1 schematically shown in FIG. 1 comprises an elongated housing 2 extending along the main axis A of the device 1. A removable cap 4 is disposed at the front end 3 of housing 2 and has an exit opening 5 for the tip 6 of a lancet 7.

The lancet 7 is held by a lancet holder 8 in such a fashion that the position of the tip 6 relative to the holder 8 is reproducibly the same when a new lancet 7 is inserted into the holder for subsequent blood withdrawal. Other mechanisms for achieving this goal which can also be used in the present invention are disclosed in U.S. Pat. No. 5,318,584 which is hereby expressly incorporated herein by reference.

The front end 3 of the housing 2 is pressed against a body part in which a wound is to be produced in order to obtain a drop of blood. The lancet holder 8 then makes a puncturing motion to propel the lancet 7, held in the lancet holder 8, at high velocity along a predetermined puncturing path preferentially extending along the main axis A in the puncture direction symbolized by the arrow 10 until its tip 6 exits from the opening 5 and penetrates into the body part. The lancet 7 is then returned to its initial position in the return direction indicated by arrow 11.

The puncturing and return motion of the lancet holder 8 (and thereby the lancet 7) is driven by a lancet drive (designated in its entirety with 12) including a lancet drive rotor 13 borne by a rotation bearing 14 for rotation about the main axis A in a fixed axial position in the housing 2. The lancet drive rotor 13 is connected to a drive spring 15, configured as a torsion spring surrounding the drive rotor 13. One end of the drive spring 15 is attached to the lancet drive rotor 13 and the other end is attached to the housing 2.

The drive spring 15 is loaded by rotating the lancet drive rotor 13 in opposition to its spring force. In the embodiment shown, a leftward rotation of the rotor 13 (as viewed from the rear end 16 of the housing 2) is required. Of course, the components could readily be configured to require rotation in the opposite direction. This loading motion is effected by moving a loading element 17 along the main axis A toward the front end 3. In one embodiment, the loading element 17 is formed by a button 17A which projects out of the rear end 16 of the housing 2 and is loaded by a restoring spring 18 in opposition to this motion. A loading cam 20 is fixed to the loading button 17A and travels along surface 22 which runs along a helical path 21 fashioned on the drive rotor 13. The loading button 17A and the associated loading cam 20 are guided to be axially displaceable but to prevent rotation. The shape of the helical path 21 thereby leads to a transformation of the motion of the loading button 17A, along a linear loading path symbolized by arrow 23, into rotation of the lancet drive rotor 13 about a rotational axis extending parallel to the main axis A. Thus, the lancet drive rotor 13 is loaded by tensioning the drive spring 15. After loading, the lancet drive rotor 13 is locked in the loaded position using a locking device 19 (not shown in detail in FIG. 1). The loading button 17A with the cam 20 and the drive rotor 13 with the helical path 21 of surface 22 constitute the input side, designated in its entirety with 24, of a two-sided rotary/translatory transmission 25.

The output side 26 of transmission 25 is configured to convert, after the lancet drive 12 is triggered via a trigger button 27 (the function of which is not shown in FIG. 1), the rotational motion of the lancet drive rotor 13, driven by the drive spring 15, into puncturing motion in direction 10 along the main axis A. This is done using a cam mechanism 28 comprising a cam guide 30 and a guide pin 31 fitting into the cam guide 30. The guide pin 31 is fixed to the lancet holder 8 and the lancet holder 8 is borne such that it may be displaced axially, but not rotated. The cam guide 30 is fashioned by a recess 32 in the lancet drive rotor 13. It is shaped such that during the loading motion, the guide pin 31 travels through a first section 33 of the cam guide 30 which, in the embodiment shown, is substantially straight and runs transverse to the main axis A. During the puncturing and return motions, the guide pin 31 passes through a second section 34 of the cam guide 30 which initially extends toward the front end 3 and then toward the rear end 16 to thereby effect a defined puncturing and return motion of the holder 8. Further details concerning this type of structure can be taken from the above mentioned U.S. Pat. No. 5,318,584 showing a design in which the cam guide 30 is part of the lancet holder 8 and the guide pin 31 rotates. In the present invention, these functions are preferentially reversed: the guide pin 31 is firmly attached to the lancet holder 8 for axial motion, whereas the cam guide 30 rotates with the lancet drive rotor 13.

FIGS. 2 through 8 provide differing representations of an embodiment of a blood withdrawal device in accordance with the invention. The components described with reference to FIG. 1 are designated with the same reference symbols in FIGS. 2 through 8 and will not be described again.

Figure 3:
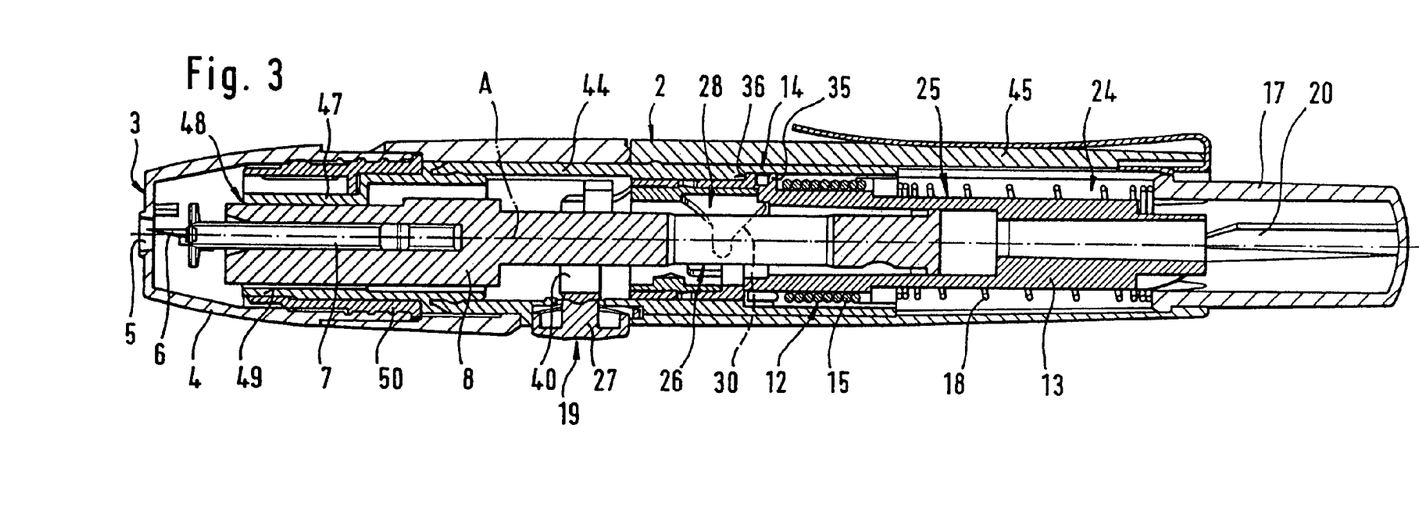
FIG. 3 is a cross-sectional view of the blood withdrawal device of FIG. 2 having a lancet inserted in the lancet holder.
Figure 4:
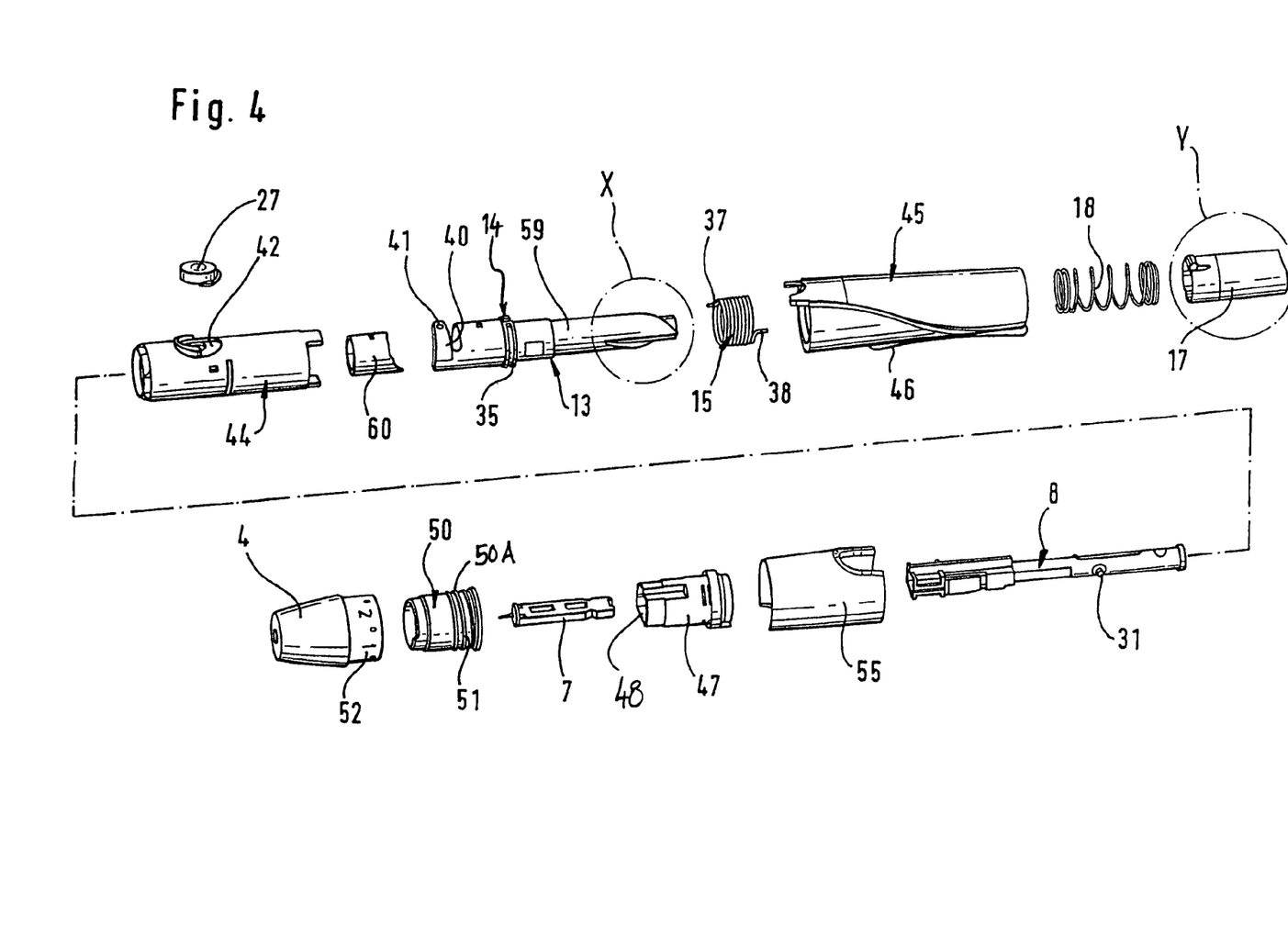
FIG. 4 is an exploded, perspective view of a blood withdrawal device in accordance with the present invention.

As shown in FIGS. 3 and 4, the rotational bearing 14 is formed by a bearing ring 35 fashioned on and protruding past the peripheral surface of the lancet drive rotor 13 and cooperating with an associated shoulder 36 of the housing 2. The bearing ring 35 has an interruption into which a first leg 37 of the drive spring 15 engages. A second leg 38 is fixed to the housing 2.

Figure 2:
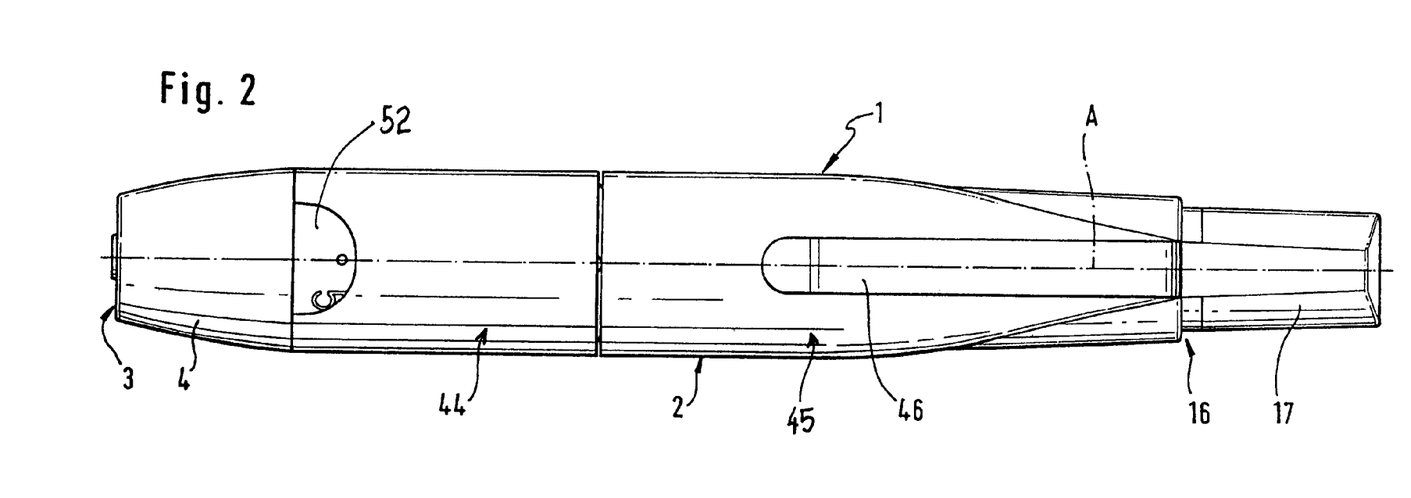
FIG. 2 is another side view of a blood withdrawal device.

Referring now to FIGS. 2 through 4, the lancet drive 12 is surrounded by two axially joinable housing portions: a front housing portion 44 and a rear housing portion 45. The blood withdrawal device 1 can, for example, be secured within a suit jacket pocket using a clip 46 disposed on the rear housing portion 45. A lower insert member 47 is inserted into the front housing portion 44 and has a central axial opening 48 whose inner shape corresponds to the outer shape of the lancet holder 8. The walls of the axial opening 48 provide a precise guide 49 (FIG. 3) for the puncturing and return motion of the lancet holder 8 and thus of the lancet 7.

The lower end of the insert member 47 is surrounded by an adjustment ring 50 having a thread 50A (FIG. 4) provided on its outer surface 51 onto which the cap 4 is screwed. The longitudinal position of the cap 4 relative to the lancet holder 8 can be changed to adjust the puncturing depth through rotation of the cap 4 relative to the adjustment ring 50. The adjustment position is indicated by a scale 52 on the cap 4.

In the embodiment shown, the locking device 19 comprises a resilient tab 40 on the lancet drive rotor 13. A short locking pin 41 (FIG. 4) extends radially outwardly past the resilient tab 40 to engage an associated opening 42 of the front housing portion 44 and lock the lancet drive in the loaded state of the spring 15. For triggering, the trigger button 27 is pressed at its lower triggering end into the opening 42 to free the locking pin 41. The trigger button 27 is preferentially transparent so that the locking pin 41, and optionally, portions of the resilient tab 40 can be viewed through the trigger button 27 in the loaded state of the locking pin 41. These components are preferentially given a contrasting color (e.g., yellow or red) to provide simple recognition of the loaded state of the blood withdrawal device 1.

The front housing portion 44 and the cap 4 are partially surrounded by an ejection sleeve 55, shown only in FIG. 4. The ejection sleeve 55 can expel the lancet 7 from the holder 8 after the cap 4 and the adjustment ring 50 are removed from the lower end of the housing 2.

Figure 5:
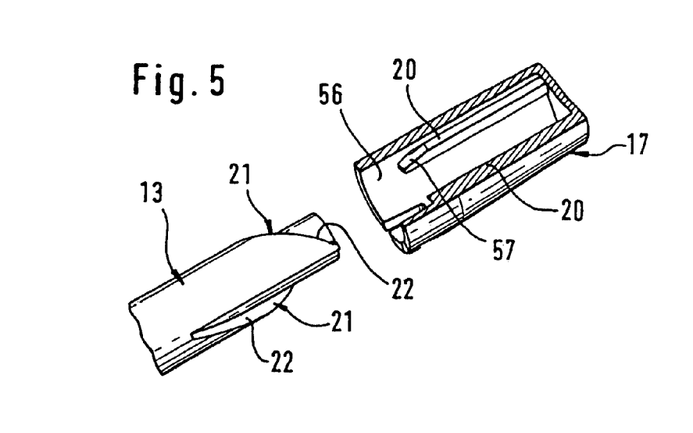
FIG. 5 is a partially fragmented, perspective view of a rearward end of a lancet drive rotor shown in FIG. 4 and of a loading element shown in FIG. 4, wherein the latter is sectioned.
Figure 6:
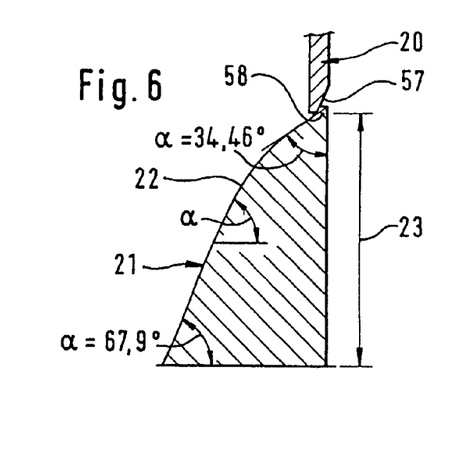
FIG. 6 is an unfolded, planar representation of the loading sleeve helical path shown in FIGS. 2 and 3.
Figure 7:
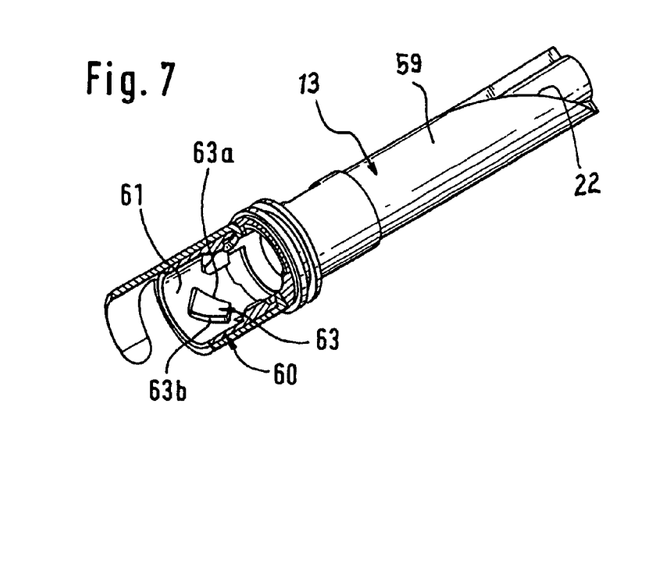
FIGS. 7 and 8 are perspective views, partly in section, of a loading sleeve shown in FIG. 4 with an inserted cam guide bushing.

FIGS. 5 and 6 illustrate details of the input side 24 of the two-sided rotary/translatory transmission 25. As can be seen in FIG. 5, two helical paths 21 with parallel running surfaces 22 are fashioned on the rear end of the lancet drive rotor 13 and cooperate with associated loading cams 20 disposed on the inner wall 56 of the loading button 17A. During loading, the loading cams 20 each move along the surfaces 22 of the helical path 21 with their diagonally slanted or sloped contact surfaces 57.

FIG. 6 best shows a configuration in which the slope of the helical path 21 (i.e., the angle α between the surface 22 and a straight line perpendicular to the main axis and passing through the surface 22 at the respective point) varies in the direction of the loading motion 23. The angle α preferentially increases, at least in sections, along the length of the helical path 21 (corresponding to the direction of the loading motion 23 of cam 20) in the direction in which the cam 20 travels during the loading motion 23. In a particularly preferred embodiment, this increase is continuous. In the exemplary embodiment shown in FIG. 6, the angle α is approximately 68° at the end of the helical path 21 and approximately 34.5° at the start. The slope should change in such a fashion that, during loading, the force which has to be exercised on the loading button 17A is substantially constant at least in sections as button 17A is moved through its path of travel in the direction of loading motion 23. Since the restoring force of the drive spring 15 increases during the loading process, the transmission ratio of the input side 24 of the rotary/translatory transmission 25 should be relatively large at the beginning of the loading process and decrease continuously in one direction of the loading motion 23. This may be achieved by increasing the slope angle α.

The contact surface 57 of loading cam 20 is preferentially slanted in such a fashion as to assure area contact with the helical path 21 at least along a portion of the second half of the length of the helical path 21 traveled by cam 20 during loading. In the embodiment shown in the figures, the slant of the contact surface 57 is equal to the slope of the surface 22 in the front section (lower section in FIG. 6) thereof. This facilitates a particularly smooth sliding and low wear in that region of the loading process which has the highest opposing forces of the drive spring 15.

The helical path 21 has a ramped starting section 58 fashioned to reduce stress associated with the initial contact of a loading cam 20, configured in the above described fashion, on the surface 22 of the helical path 21. The starting section 58 has a slope which corresponds to that of the surface 22. Although the contact surface of the loading cam 20 at the lower end of the ramp-shaped starting section 58 briefly contacts only along a narrow line, excessive wear does not occur in this region due to the low spring force.

The choice of material used for the lancet drive rotor 13 (at least the surface 22 thereof) and for the loading cam 20 (at least the contact surfaces 57 thereof) affects the ease of operation of device 1. The former preferentially comprises a plastic based on polyacetal material, in particular, based on a polyoxymethylene (POM). A styrene-acrylnitril-copolymer (SAN) based plastic is particularly well-suited for the latter.

As shown in FIGS. 3, 4, 7 and 8, the lancet drive rotor 13 consists essentially of two parts: a loading sleeve 59 and a cam bushing 60. The cam bushing 60 can be inserted into the loading sleeve 59 from the front. The front end of the loading sleeve 59, with the cam bushing 60 inserted therein, surrounds the rear end of the lancet holder 8 in the region in which the lancet holder 8 has two diametrically opposed guide pins 31. The loading sleeve 59 and the cam bushing 60 inserted therein form two recesses 61, 62 in the lancet drive rotor 13 whose bordering edges together define a cam guide. The recesses 61 and 62 are fashioned in such a manner that during each phase of the rotational motion, one of the recesses 61 guides a guide pin 31 rearwardly and the other recess 62 guides a guide pin 31 forwardly.

In the embodiment shown, the rear edge 63a of the raised area 63 (see in FIG. 7) limits the motion of a guide pin 31 during the return phase in a forward direction. Thus, motion of the lancet holder 8 in the forward direction is limited by the rear edge 63a of the raised area 63. The forward edge 63b of the raised area 63 similarly limits motion of the lancet holder 8 toward the rear during the puncturing and return phase.

Figure 8:
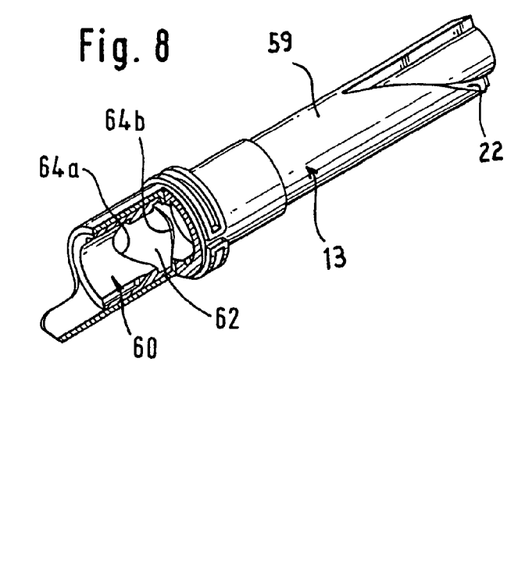
Figure 9:
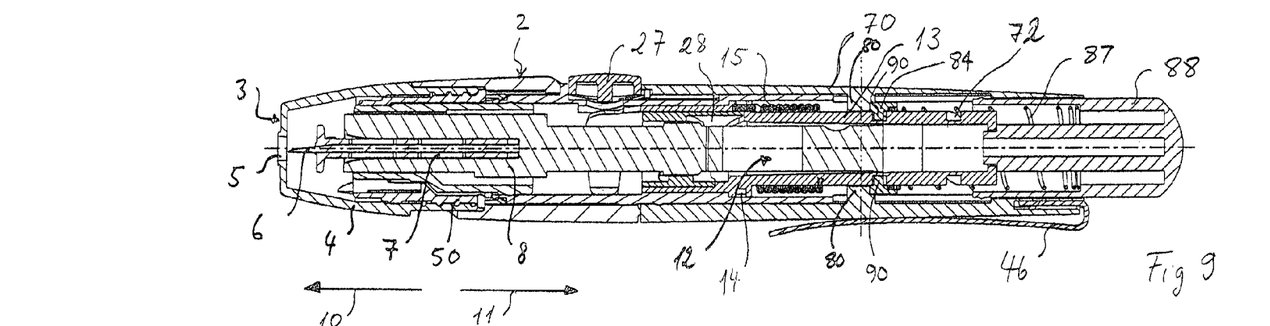
FIG. 9 is a side, cross-sectional view of another embodiment of a blood withdrawal device having a lancet inserted in the lancet holder.
Figure 10:
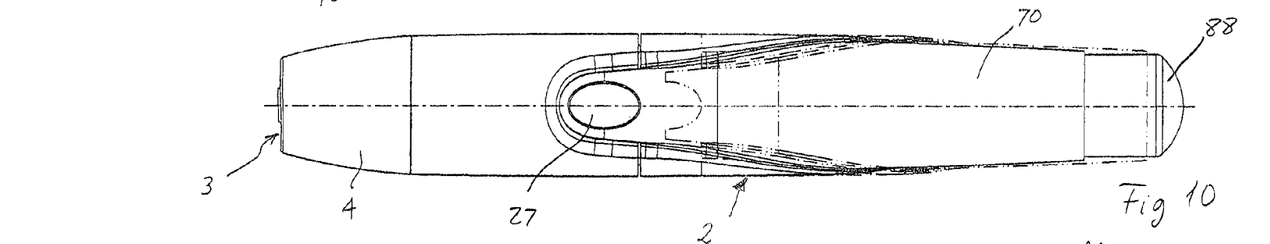
FIG. 10 is a side view of the blood withdrawal device of FIG. 9.

During the puncturing and return phase, the freedom of motion of the lancet holder 8 in the forward direction is limited by the upper edge 64a of the cam bushing 60 (visible in FIG. 8). As also shown in FIG. 8, the front edge 64b formed in the cam bushing 60 limits the freedom of motion of the lancet holder 8 in the rear direction during the loading procedure.

Taken together, the edges 63a, 63b, 64a and 64b of the recesses 61 and 62 fashioned in the inner wall of the lancet drive rotor 13 thereby constitute a cam guide through which the two guide pins 31 travel.

In the blood withdrawal device shown, both the helical surface 22 and the cam guide of the drive rotor 13 are fashioned on a single rigid component (comprising two parts, namely the loading sleeve 59 and the cam bushing 60), for manufacturing reasons only. Other configurations are possible in which the rotational coupling between the cam guide 30 and the helical path surface 22 is effected indirectly (e.g., via a connection rod). Regardless of its construction details, the drive rotor 13 rotates about the main axis A, independent of whether it consists of one or a plurality of components.

In one embodiment, the loading cam 20 is fashioned as an integral part of the loading button 17A. As should be apparent to one of ordinary skill in the art, other designs are possible in which the loading cam 20 and the loading button 17A are separate components. In such alternate embodiments, when the loading element 17 is operated, the loading cam 20 should move synchronously with the loading button 17A along the direction of the linear loading motion 23.

The blood withdrawal apparatus in accordance with the invention can have a very slender shape. Preferably the blood withdrawal device should have a maximum diameter of less than 20 mm. Use of a design in accordance with the invention even allows values of less than 15 mm.

Such a slender shape permits easy carrying of the blood withdrawal device. It also allows a very low rotational moment of inertia for the lancet drive rotor 13. This low rotational moment of inertia permits loading of the lancet drive 13 with a loading force of only approximately 11 Newton through a loading path of 15 mm using a relatively weak drive spring 15 having a spring constant between approximately 25 to 35 Nmm. Despite ease of operation, the device 1 provides extremely rapid and precise movement for the lancet with low vibration and minimal associated pain.

Figure 11:
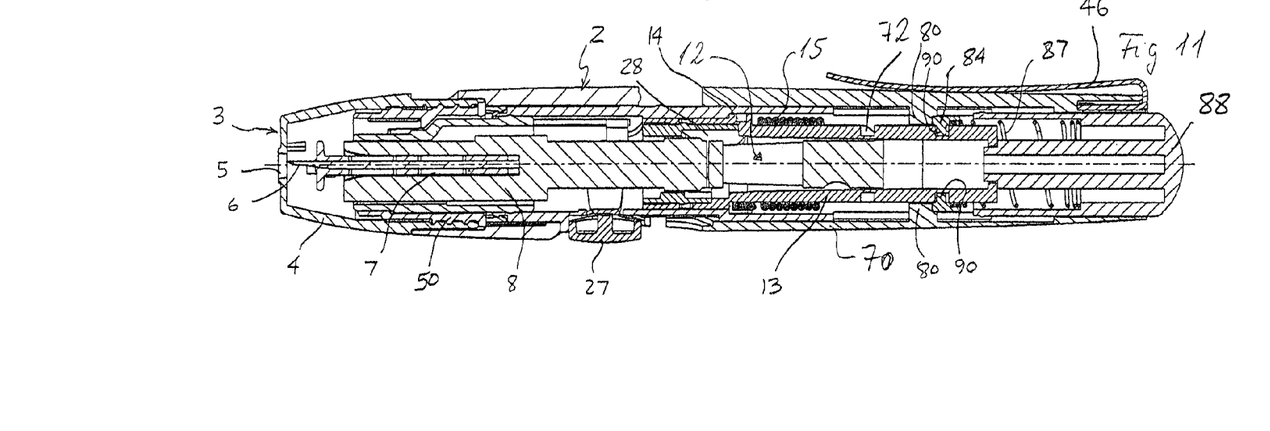
FIG. 11 is a side, cross-sectional view similar to FIG. 9.
Figure 12:
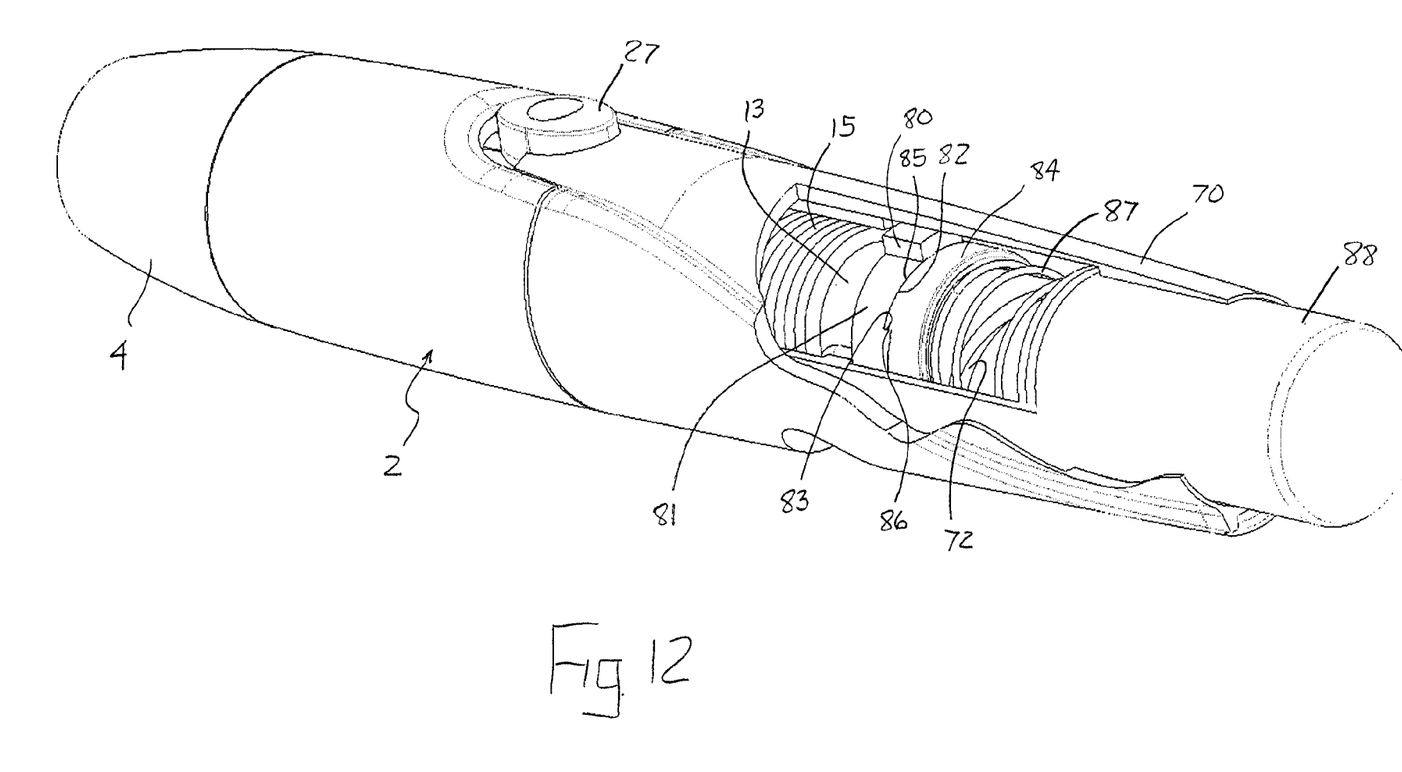
FIG. 12 is a partially fragmented, perspective view of the blood withdrawal device of FIG. 9.

The embodiment shown in FIGS. 9 to 12 is similar to the embodiment shown in FIGS. 2 to 8. Corresponding parts are designated by the same reference numerals. Deviating from the previously described embodiment, the loading element of the device shown in FIGS. 9 to 12 is embodied as a sleeve 70 substantially encircling the rear part of housing 2. Sleeve 70 includes inwardly projecting tabs 80 which are connected together by ring 81 (see FIG. 12). Ring 81 encircles rotor 13 and has an inner diameter that is slightly larger than the outer diameter of rotor 13. Ring 81 further includes a drive surface 82 having at least one stop surface 83 as best shown in FIG. 12. A cam 84 also encircles rotor 13 and includes a cam surface 85 and a stop surface 86 that mate with drive surface 82 and stop surface 83, respectively. Cam 84 further includes inwardly projecting cam tabs 90 that extend from an inner surface of cam 84 into a helical groove 72 formed in an outer surface of rotor 13. A return spring 87 extends between a button 88 and cam 84. Spring 87 biases cam 84 (and sleeve 70) toward the uncocked position shown in FIGS. 9 and 12 (and in solid lines in FIG. 10).

In order to load lancet drive 12 by drive spring 15, sleeve 70 of housing 2 is pulled backwards from its uncocked position (i.e., in return direction 11). As sleeve 70 is moved in direction 11, cam 84, which is locked against rotation by the engagement between stop surfaces 83 and 86, is pulled rearwardly. Cam tabs 90 move along the helical path defined by helical groove 72 of drive rotor 13. Helical groove 72 is similar to that of the earlier described embodiment, but is formed in a reciprocal manner (i.e., the path traveled by cam tabs 90 starts at a point closer to the front end of the device and ends at a point closer to the opposite rear end of the device). Otherwise, the operation is the same: rotor 13 borne by rotation bearing 14 rotates about the main axis A in a fixed axial position in the housing 2 during the pulling of sleeve 70 (i.e., as a result of the travel of cam tabs 90 through helical groove 72). The extended or cocked position of sleeve 70 is shown in FIG. 11.

After the loading action is terminated, sleeve 70 is returned to its uncocked position by return spring 87. More specifically, return spring 87 pushes cam 84 in direction 10 through helical groove 72. The configuration of stop surfaces 83 and 86 permits rotation of cam 84 relative to ring 81. Accordingly, cam 84 rotates through helical groove 72 while rotor 13 remains fixed against rotation in its cocked position. As cam 84 rotates, it also moves in direction 10, thereby moving ring 81, and sleeve 70, which is connected thereto, in direction 10 into the uncocked position.

Since rearwardly oriented button 74 of FIGS. 9 to 12 is not required for the loading action, it can be used for other purposes such as pushing lancet 7 out of lancet holder 8 after use.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

What is claimed is:

1. A lancet device, comprising:
   a housing;
   a lancet disposed in the housing and configured for puncturing movement relative to the housing;
   a spring;
   a transmission having a rotor coupled to the spring; and
   a loading element coupled to the transmission and configured for loading movement along an axial loading path relative to the housing;
   wherein, the transmission converts the loading movement of the loading element into a first rotation of the rotor about an axis disposed substantially parallel to the axial loading path, the first rotation tensioning the spring and thereby loading the lancet device.

2. The device of claim 1, wherein the spring is configured to drive the rotor into a second rotation, the transmission converting the second rotation into translational movement of the lancet relative to the housing.

3. The device of claim 1, wherein the loading element includes a cam that engages a surface of the rotor during the loading movement of the loading element, thereby rotating the rotor.

4. The device of claim 3, wherein the cam travels in a helical groove formed on an outer surface of the rotor during the loading movement of the loading element.

5. The device of claim 3, wherein the loading element includes a sleeve that substantially encircles a portion of the housing, the sleeve including a drive surface for engaging the cam.

6. The device of claim 5, wherein the drive surface includes a stop surface that mates with a corresponding stop surface formed on the cam to prevent rotation of the cam during movement of the loading element during loading.

7. The device of claim 3, wherein the surface defines a helical path.

8. The device of claim 7, wherein the helical path extends along an outer surface of the rotor.

9. The device of claim 7, wherein the helical path has a slope that increases in the direction of the loading cam movement.

10. The device of claim 9, wherein the slope varies such that a loading force required for moving the loading element from a first position to a second position during loading is substantially constant.

11. The device of claim 1, wherein the loading element comprises a button.

12. The device of claim 1, wherein the loading element includes a sleeve mounted on an outer surface of the housing.

13. The device of claim 12, wherein the sleeve substantially encircles the housing.

14. A blood lancet device for withdrawing blood, including:
- a housing;
- a lancet being movable in the housing;
- a rotor disposed in the housing and having a spring connected thereto;
- a locking device for locking the spring in a loaded state; and
- a transmission connected to the housing, the transmission converting a linear motion of a loading element into a first rotational motion of the rotor about a rotational axis that is substantially parallel to a main axis of the housing to load the rotor by tensioning the spring.

15. The device of claim 14, wherein the transmission converts a second rotational motion of the rotor driven by the spring into movement of the lancet in the direction of the main axis of the housing along a puncturing path.

16. The device of claim 14, wherein the loading element includes a cam that engages a surface of the rotor during the linear motion of the loading element, thereby rotating the rotor.

17. The device of claim 16, wherein the cam has a tab that travels in a helical groove formed on an outer surface of the rotor during the linear motion of the loading element.

18. The device of claim 17, wherein the helical path has a slope that increases in the direction of the cam movement.

19. The device of claim 18, wherein the slope varies such that a loading force required for moving the loading element from a first position to a second position during loading is substantially constant.

20. The device of claim 16, wherein the loading element includes a sleeve that substantially encircles a portion of the housing, the sleeve including a drive surface for engaging the cam.

21. The device of claim 20, wherein the drive surface includes a stop surface that mates with a corresponding stop surface formed on the cam to prevent rotation of the cam during movement of the loading element during loading.

22. The device of claim 16, wherein the surface defines a helical path.

23. The device of claim 22, wherein the helical path extends along an outer surface of the rotor.

24. The device of claim 14, wherein the loading element comprises a button connected to one end of the housing.

25. The device of claim 14, wherein the loading element includes a sleeve mounted on an outer surface of the housing.

26. The device of claim 25, wherein the sleeve substantially encircles the housing.

27. The device of claim 14, wherein the loading element moves along a loading element axis that is substantially parallel to the main axis of the housing.

* * * * *